United States Patent [19]

Foster et al.

[11] Patent Number: 5,071,857

[45] Date of Patent: * Dec. 10, 1991

[54] 2,6-DIOXOPIPERIDINE DERIVATIVES, THEIR PREPARATION AND PHARMACEUTICAL COMPOSITIONS CONTAINING THEM

[75] Inventors: Allan B. Foster, Carshalton Beeches; Michael Jarman, London; Grahame N. Taylor, Cowley; Chui-Sheung Kwan, Epsom, all of England

[73] Assignee: National Research Development Corporation, England

[*] Notice: The portion of the term of this patent subsequent to May 26, 2004 has been disclaimed.

[21] Appl. No.: 571,830

[22] PCT Filed: Dec. 10, 1984

[86] PCT No.: PCT/GB84/00425
§ 371 Date: Jul. 16, 1985
§ 102(e) Date: Jul. 16, 1985

[87] PCT Pub. No.: WO85/02618
PCT Pub. Date: Jun. 20, 1985

Related U.S. Application Data

[63] Continuation of Ser. No. 761,589, Jul. 16, 1985, abandoned.

[30] Foreign Application Priority Data

Dec. 9, 1983 [GB] United Kingdom ............... 8332954
Nov. 30, 1984 [GB] United Kingdom ............... 8430451

[51] Int. Cl.$^5$ ............... A61K 31/445; C07D 401/04
[52] U.S. Cl. ............... 514/318; 546/193
[58] Field of Search ............... 546/193; 514/318

[56] References Cited

U.S. PATENT DOCUMENTS 2,673,205  3/1954  Hoffmann et al. ............... 260/281
2,848,855  8/1958  Hoffmann et al. ............... 260/281
3,057,867  10/1962 Taub ............... 260/281
4,668,689  5/1987  Foster et al. ............... 546/193

OTHER PUBLICATIONS

Knabe, et al., Arch. Pharm., 317, pp. 514–619, (1984).

Smith, et al., British Medical Journal, 283, pp. 1432–1434, (1981).
Carelli, Ann. Chim., (Rome), 51, pp. 713–718, (1981).
Graves, et al., Endocrynology, 105, pp. 52–57, (1979).
Tagmann, et al., Helv. Chim. Acta., 35, pp. 1541–1548, (1952).
Hoffmann, et al., Helv. Chim. Acta., 46, pp. 387–394, (1957).
Kukolja, et al., Croatica Chimica ACta., 33, pp. 41–44, (1961).
Paul, et al., J. Med. Chem., 17, pp. 539–541, (1972).
Pifferi, et al., J. Med. Chem., 18, pp. 741–746, (1975).
Hoeffken, et al., Cancer Treatment Reports, 70, pp. 1153–1157 (1986).
Smith, et al., Cancer Research (Suppl.) 42, pp. 34305–34335 (1982).
Coombes, et al., Lancet, (Dec. 1, 1984), pp. 1237–1239.
Santen, et al., J. Clin. Endocrin., 45, pp. 469–479 (1977).
Camacho, et al., J. Pediatr., 68, pp. 852–853 (1966).
Griffiths, et al., Cancer, 32, pp. 31–37 (1973).
Foster, et al., J. Med. Chem., 26, pp. 50–54 (1983).

Primary Examiner—Joseph Paul Brust
Attorney, Agent, or Firm—Rosenman & Colin

[57] ABSTRACT

In the treatment of estrogen-dependent tumors, it is desirable to improve the therapy obtainable from the compound aminoglutethimide. It has now been found that 3-ethyl-3-(4-pyridyl)glutarimide and derivatives thereof of formula

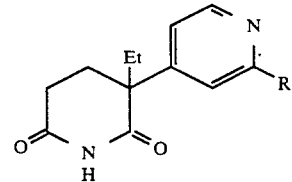

wherein R represents a hydrogen atom or an alkyl group having 1 to 4 carbon atoms offers advantages over aminoglutethimide. 3-Ethyl-3-(4-pyridyl)glutarimide can be prepared by various ring-closing reactions, especially by heating 4-(4-pyridyl)-hexano-1,4-dinitrile with a strong mineral acid.

8 Claims, No Drawings

2,6-DIOXOPIPERIDINE DERIVATIVES, THEIR PREPARATION AND PHARMACEUTICAL COMPOSITIONS CONTAINING THEM

This application is a continuation of Ser. No. 06/761,589, filed July 16, 1985, now abandoned.

BACKGROUND OF THE INVENTION

1. Field of Invention

This invention relates to derivatives of 2,6-dioxopiperidine, also known as glutarimide, their preparation and pharmaceutical compositions containing them.

2. Description of Prior Art

U.S. Pat. No. 2,673,205 (Ciba) claims 3,3-disubstituted-glutarimides of formula

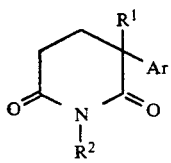

(1)

$R^1$ represents an aliphatic hydrocarbyl group of 1 to 6 carbon atoms and Ar represents a phenyl or pyridyl group, and $R^2$ represents hydrogen or a substituent group such as alkyl, acyl, phenyl or benzyl. 12 such compounds were prepared, 11 of them being 3-phenyl derivatives (Ar in formula 1=phenyl) and 3-ethyl-3-(3-pyridyl)glutarimide of formula

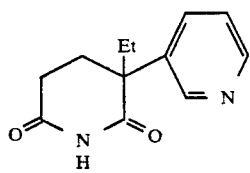

(2)

where Et=ethyl. The class of compounds claimed in U.S. Pat. No. 2,673,205 is stated to have an anti-convulsive effect. However, the preferred compound, 3-ethyl-3-phenylglutarimide was subsequently marketed as the sedative and hypnotic agent glutethimide. The later U.S. Pat. No. 2,848,455 (Ciba) claims 3-methyl and -ethyl-3-(4-aminophenyl)glutarimides as anti-convulsive agents. The 3-ethyl compound is known as aminoglutethimide. V. Carelli, Ann. Chim. (Rome) 51, 713–718 (1961), describes "Nota", 3-ethyl-3-(2-pyridyl)glutarimide, as having a sedative and hypnotic effect. U.S. Pat. No. 3,057,867 claims a large class of N-aminoglutarimides having sedative and anti-convulsive activity.

The present invention is concerned with an entirely different field of therapy, namely anti-cancer therapy, specifically the treatment of oestrogen-dependent tumors. Such tumors are most commonly produced in the breast tissue of female mammals. Within the last 5 years or so aminoglutethimide has come seriously into the reckoning for treatment of advanced breast cancer in post-menopausal patients. Its advantages over tamoxifen have been set out in a recent paper by I. E. Smith et al., British Medical Journal, 283, 1432–1434 (1981). One important factor in the success of aminoglutethimide in this connection is its ability to inhibit in vivo the activity of the enzyme aromatase in peripheral tissue. This enzyme is required for the conversion of androgens into oestrogens. Aminogluthethimide therefore breaks the metabolic pathway to oestrogens. Unfortunately, however, aminoglutethimide also inhibits the enzyme desmolase which is required for the metabolic conversion of cholesterol to corticosteroids. Since the body needs corticosteroids, treatment with aminoglutethimide has to be supplemented by cortisone replacement therapy. Furthermore, depletion of corticosteroids causes a reflex rise in adrenocorticotrophic hormone (ACTH) which stimulates the conversion of cholesterol to pregnenolone by the enzyme desmolase and consequently the production of oestrogen precursors.

SUMMARY OF THE INVENTION

After extensive experiments, we have now found a glutarimide which inhibits aromatase but not desmolase. Moreover, tests indicate that its sedative and anti-convulsant side-effects are lower than that of aminoglutethimide. We have found that the compound can be used successfully in the treatment of mammalian breast cancer. The compound is 3-ethyl-3-(4-pyridyl)glutarimide. Also, certain derivatives thereof, having a substituent group in the pyridine ring ortho to the N-atom inhibit aromatase and show no or insignificant inhibition of desmolase. These compounds are believed to be novel and accordingly the invention provides these compounds which collectively are of general formula

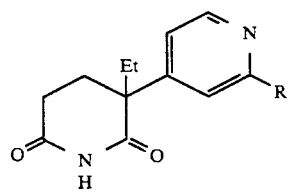

(3)

wherein R represents a hydrogen atom or an alkyl group having 1 to 4 carbon atoms (which can have a straight or branched chain in the case of propyl and butyl), and their acid addition salts, both per se and for use in the treatment of oestrogen-dependent tumors in mammals.

The compounds of formula (3) are optically active. The invention includes them in the form of their individual optical isomers and mixtures thereof, especially racemates. The R isomers [cf. the R isomer of aminoglutethimide, Graves and Salhanick, Endocrinology 105, 52 (1979)] are expected to show the greater inhibition of aromatase.

The invention can be considered as one of selection with respect to the above-mentioned generic disclosure of 3-ethyl-3-pyridylglutarimides. Our tests for desmolase and aromatase activity have shown that of the three isomeric pyridyl compounds only that with the ring-nitrogen in the 4- position of the pyridine ring is an aromatase inhibitor, with no effect on desmolase. Those with the ring nitrogen in the 2- or 3- position are ineffective against both aromatase and desmolase.

Moreover, many other glutarimides which we have tested do not have the desired property, i.e. of inhibiting aromatase but having no significant effect on desmolase. The properties found can be summarized as follows (+++=strong inhibition; +=weak inhibition; o=no significant effect):-

|  | Desmolase inhibition | Aromatase inhibition |
|---|---|---|
| aminoglutethimide, i.e. 3-ethyl-3-(4-aminophenyl)glutarimide | + + + | + + + |
| "m-aminoglutethimide", i.e. 3-ethyl-3-(3-aminophenyl)glutarimide | + + + | + |
| 5-amino-3-ethyl-3-phenylglutarimide | o | o |
| N-aminoglutethimide, i.e. 1-amino-3-ethyl-3-phenylglutarimide | + + + | o |

The present invention also provides a pharmaceutical composition which comprises a therapeutically effective amount of a compound of formula (3) or an acid addition salt thereof in association with a pharmaceutically acceptable carrier or diluent.

3-Ethyl-3-(4-pyridyl)glutarimide can be prepared by a process which comprises reacting a compound of formula:

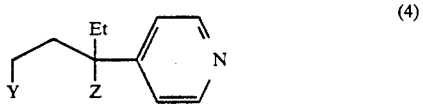

(4)

wherein Et=ethyl, each of Y and Z independently represents a carboxylic acid group or a ring closing, reactable derivative group thereof or a precursor or such an acid or derivative group and at least one of Y and Z represents an amide group or precursor thereof, under conditions effective to bring about ring closure between the amide group and the said carboxylic acid or derivative group thereof (which might or might not also be an amide group), whereby a piperidine-2,6-dione ring is formed.

The lower alkyl derivatives of formula (3) can be prepared by (a) N-oxidation of the pyridine ring followed by (b) reaction of the N-oxide under free radical-generating conditions, with a compound capable of generating the appropriate alkane free radicals, followed by reduction of the N-oxide group.

DESCRIPTION OF THE PREFERRED EMBODIMENTS

Referring to the preparation of 3-ethyl-3-(4-pyridyl)-glutarimide and to formula (4) above, one of Y and Z is conveniently an amide group or a cyano (CN) group. The cyano group is a precursor of the amide group, being convertible thereinto by the action of strong mineral acid, and the conditions required will normally include providing the strong mineral acid and preferably also heating. The other one of Y and Z can also be amide or cyano, in which case the conditions will of course include provision for hydrolysis of the amide. Where the other one of Y and Z is a carboxylic acid group or a non-amide derivative thereof, e.g. an ester, preferably a methyl or ethyl ester, heat will normally be required to effect the ring closure. Other reactive derivative groups such as acid chloride or azide, for example, will also be usable under appropriate conditions. Many analogous such ring closure reactions have been described, e.g. by E. Tagmann et al., Helv. Chem. Acta 35, 1541 (1952), K. Hoffmann et al., ib id., 46, 387 (1957), U.S. Pat. Nos. 2,673,205 and 2,848,455, S. Kukolja et al., Croatica Chimica Acta 33, 41 (1961) R. Paul et al., J. Med. Chem., 17, 539 (1972) and G. Pifferi et al., J. Med. Chem. 18, 741 (1975). Appropriate conditions can therefore be deduced by those skilled in the art.

A preferred procedure of the present invention comprises heating 4-(4-pyridyl)hexano-1,4-dinitrile with a strong mineral acid, e.g. sulfuric and/or hydrochloric acid, so as to bring about amide formation and thereafter ring-closing the amide under hydrolysis conditions and separating the desired 3-ethyl-3-(4-pyridyl)glutarimide from the reaction mixture.

The starting dinitrile can be prepared by reacting 2-(4-pyridyl)-butyronitrile with acrylonitrile. 2-(4-Pyridyl)butyronitrile is a known compound which can be prepared in various ways. For example it can be prepared by reaction of 4-pyridylacetonitrile with sodium hydride or sodamide, followed by ethyl iodide or bromide. Ethylation can occur at both hydrogens of the alpha-carbon atom, leading to the unwanted, diethylated compound 2-ethyl-2-(4-pyridyl)-butyronitrile. This can be separated, e.g. by chromatography, or the mixture thereof with the desired, monoethylated compound, 2-(4-pyridyl)butyronitrile can be subjected to the reaction with acetonitrile and ring-closure as described above and the unwanted by-product separated at the end of the synthesis. Alternatively 2-(4-pyridyl)-butyronitrile can be prepared as described by M. P. Sammes et al., J. Chem. Soc., Perkin I, 2746 (1981). This synthesis involves a reaction under anhydrous conditions between N-triphenylpyridinium tetrafluoborate (easily prepared from commercially available triphenyl-carbenium tetrafluoborate) and the lithium derivative of butyronitrile (prepared by reaction of butyronitrile with n-butyl lithium and diisopropylamine).

Acid addition salts, e.g. the hydrochloride, can be prepared by conventional methods.

The preferred alkyl derivative of formula (3) is the t-butyl derivative, since it is more easily preparable than the primary and secondary alcohols by the chosen free radical route. This route of preparation involves oxidation to the N-oxide, e.g. in a manner known in itself for analogous compounds and then reaction thereof under free radical-generating conditions, e.g. in the presence of potassium peroxysulphate, with a compound capable of generating alkane free radicals, e.g. a lower alkane carboxylic acid having from 2 to 5 carbon atoms. The 2-substituted N-oxide resulting is easily hydrogenated to regenerate the pyridine ring N-atom.

3-Ethyl-3-(4-pyridyl)glutarimide is normally prepared in racemic form and the optical isomers can be resolved, if desired, by conventional methods, for example by preparation and separation of tartrate salts and re-liberation of the optically active free base. Alternatively the dinitrile precursor, i.e. 4-(4-pyridyl)-hexano-1,4-dinitrile, can be resolved into its optical isomers and the ring-closing preparative reaction carried out on the desired isomer to yield the corresponding optical isomer of the glutarimide product.

The composition of the invention can, for example, be in a form suitable for parenteral (e.g. intravenous, intramuscular or intracavitary), oral, topical or rectal administration. Particular forms of the composition may be, for example, solutions, suspensions, emulsions, creams, tablets, capsules, liposomes or micro-reservoirs, especially compositions in orally ingestible or sterile injectable form. The preferred form of composition contemplated is the dry solid form, which includes capsules, granules, tablets, pills, boluses and powders. The solid carrier may comprise one or more excipients, e.g. lactose, fillers, disintegrating agents, binders, e.g.

cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient. The present invention includes a method of treating oestrogen-dependent tumors in the mammalian body which comprises administering a compound of the invention to a mammalian patient in a therapeutically effective dose, e.g. in the range 5-50 mg/kg body weight, administered daily during the course of the treatment.

In addition to its use as a single agent, a compound of the invention could be co-administered with, administered in sequence with, or contained in a mixed formulation with other compatible agents effective against tumors of the kind described, e.g. amino-glutethimide, tamoxifen or danazol. It can also be used as a component of a combined modality treatment, for example including radiotherapy and/or surgery.

The following Examples illustrate the invention.

EXAMPLE 1

Preparation of 3-ethyl-3-(4-pyridyl)-2,6-piperidinedione

A solution of potassium cyanide (25 g) in water (133 ml) and of 4-picolyl chloride hydrochloride (30 g) in reagent grade methanol (268 ml) was heated under reflux for 2 hours, concentrated under vacuum, diluted with water (500 ml) and extracted with $CHCl_3$ (4×100 ml). Distillation of the extract afforded a single fraction of 4-pyridylacetonitrile (8.026 g), b.p. 84° C. at 0.15 mm Hg. This was dissolved in dry dimethylformamide (130 ml) and stirred with sodium hydride (3.4 g, 50% w/v dispersion in oil) for 2.5 hours. Ethyl iodide (5.7 ml, 1.93 g/ml) was added slowly with cooling and stirring. After 18 hours, excess solvent was evaporated off, the residue diluted with water (150 ml) and extracted with diethyl ether (3×300 ml). Flash chromatography (Merck Art 9385, $CHCl_3$, 4.5×15 cm column) of the extract afforded a mixture of 2-(4-pyridyl)butyronitrile and 2-ethyl-2-(4-pyridyl)-butyronitrile (9.85 g). Acrylonitrile (4.46 ml) in t-butanol (5.5 ml) was added to a solution of the above mixture in t-butanol (18 ml) and "Triton B" (0.32 ml) with cooling and stirring. ("Triton" is a Registered Trade Mark in the UK and many other countries). After 2 hours, excess solvent was evaporated off, the residue diluted with water (150 ml) and extracted with $CHCl_3$ (2×50 ml). Flash chromatography of the extract ($CHCl_3$, 4.5×15 cm column) afforded a mixture of 2-ethyl-2-(4-pyridyl) butyronitrile and 4-cyano-4-(4-pyridyl)hexanonitrile (8 g). This mixture was heated under reflux with glacial acetic acid (15 ml) and conc. sulfuric acid (3 ml) during 0.5 hours, then with addition of 5N hydrochloric acid (15 ml) for a further 3 hours, cooled, diluted with water, adjusted to pH 7-7.5 with sodium hydrogen carbonate and extracted with methylene chloride. Elution from a column (4.5×30 cm) of silica gel (Merck, Kieselgel 6) with $CHCl_3$ afforded the title compound, 2.95 g; (20% yield based on 4-pyridylacetonitrile) which crystallized from toluene, m.p. 138°-139° C. (corrected); mass spectrum, isobutane chemical ionization [$MH^+$] at m/z=219: IR (KCl) $cm^{-1}$ 2990 (CH aromatic phenyl), 2800 (NH), 1720, 1784 (C=0 imide), 1605 (C=C, aromatic phenyl); $^1$H-NMR ($CDCl_3$), δ0.87 (t,3H,$CH_3$ $CH_2$), 1.80-2.82 (m, 6H, $CH_3CH_2$, H(4), H(5)), 7.15 (d, 2H, aromatic H(3), H(5), J=4.7 Hz), 8.55 (d, 2H, aromatic H(2), H(6), J=4.7 Hz), 9.13 (br.s., 1H, NH). Anal. $C_{12}H_{14}N_2O_2$, 218.25) Calcd: C,66.03; H,6.47; N,12.84, Found: C,66.00, H,6.58; N,12.87%.

Isolation of 2-(4-pyridyl)butyronitrile 2-(4-pyridyl)butyronitrile was separated from its mixture with the diethylated by-product (2-ethyl-2-(4-pyridyl)butyronitrile), on a small scale using 0.26 g of the mixture. In a flash chromatography separation using $CHCl_3$:EtOH, 97:3 v/v as eluant, the diethylated by-product was eluted first, then a mixture and finally the required component (oil, 0.056 g). This was characterized by crystalline monopicrate (0.082 g, m.p. 127°) formed by treatment of an ethanolic solution with an ethanolic solution of picric acid (0.126 g). Anal. $C_{15}H_{13}N_5O_7$ (375.30) Calcd: C,48.00; H,3.49; N,18.67. Found: C,48.09; H,3.54; N,18.76%.

EXAMPLE 2

Tablets of the following composition are prepared:

| | | |
|---|---|---|
| Active ingredient (micronised) | 83.3% | w/w |
| "Avicel" (microcrystalline cellulose) | 12.7% | " |
| polyvinylpyrrolidone | 1% | " |
| alginic acid | 2% | " |
| magnesium stearate | 1% | " |

The active ingredient is mixed with the "Avicel" and polyvinylpyrrolidone is added. The mixture is dissolved in sufficient industrial methylated spirits 74° OP to produce a mass suitable for granulating. The mass is granulated through a 20 mesh sieve (all mesh sizes herein are British standard) and the resultant granules are dried at a temperature not exceeding 50° C. The dried granules are passed through a 20 mesh sieve and the alginic acid and magnesium stearate then added and mixed with the granules. The product is compressed into tablets.

By the same method tablets of the following formulation are prepared:

| | | |
|---|---|---|
| Active ingredient (micronised) | 62.5% | w/w |
| "Avicel" (microcrystalline cellulose) | 33.5% | " |
| polyvinylpyrrolidone | 1% | " |
| alginic acid | 2% | " |
| magnesium stearate | 1% | " |

EXAMPLE 3

Tablets of the following composition are prepared:

| | | |
|---|---|---|
| Active ingredient (micronised) | 83.3% | w/w |
| lactose (300 mesh) | 6.3% | " |
| maize starch | 5% | " |
| gelatine | 3.3% | " |
| magnesium stearate | 2% | " |

These tablets are prepared by the active ingredient with lactose and half the total quantity of maize starch required, and adding to the mass a 5% w/v solution of gelatin in water.

The products are granulated through a 16 mesh sieve, and the resultant granules dried to constant weight at a temperature not exceeding 60° C. The dried granules are passed through a 20 mesh sieve and mixed with magnesium stearate and the remainder of the maize starch. The product is compressed into tablets.

EXAMPLE 4

Preparation of
3-ethyl-3[4-2-t-butyl)pyridyl]piperidine-2,6-dione

To a solution of 3-ethyl-3-(4-pyridyl)2,6-piperinedione (0.0436 g, 0.2 mmol) in benzene (1 ml), m-chloroperbenzoic acid (0.04 g 0.3 mmol) was added. After 16 hours at room temperature, preparative TLC (CHCl$_3$: MeOH, 19:1) was used to separate the N-oxide from unreacted m-chloroperbenzoic acid and its decomposition product. The N-oxide was recrystallized from ethanol, giving large colorless prisms (0.02 g, 43%), m.p. 195°–196° C.; mass spectrum: m/z 234 [M+].

A solution of pivalic acid (262 mg, 2.56 mmol) and sodium hydroxide (68 mg, 1.7 mmol) was added to an aqueous solution (10 ml) of 3-ethyl-3-(4-pyridyl)piperidine-2,6-dione N-oxide (200 mg, 0.854 mmol) prepared as above and the mixture was heated to boiling. A solution (6 ml) of potassium peroxysulphate (230 mg, 0.854 mmol) was added dropwise to the above mixture. Heating was continued for an additional 3 hours. On cooling, the reaction mixture was neutralized with sodium hydrogen carbonate and concentrated to dryness. The dry paste was dissolved in methanol and washed through a column (15×40 mm, Merck 9385) with methanol. The eluant collected was concentrated and purified by preparative TLC plates (4, 20×20 cm, 1 mm thickness, CHCl$_3$:MeOH - 19:1). 3-Ethyl-3-[4-(2-t-butyl)pyridyl]-piperidine-2,6-dione-N-oxide (30 mg), mass spectrum: m/z 291 [M+1]+, obtained as a pale yellow oil, was put hydrogenated with 10% palladium on charcoal (100 mg) in ethanol for 16 hours, filtered and purified by a preparative TLC plate (20×20 cm, 1 mm thickness, CHCl$_3$:MeOH - 19:1). The title compound was obtained as colourless oil, mass spectrum: m/z 274[M]+.

Biochemical Tests

The activity of various glutarimides against the enzymes aromatase and desmolase was assayed as follows. Each compound was examined over a range of concentrations. At each concentration of inhibitor, samples were removed at three time points. The results were plotted on a graph of product released against time of incubation. The resulting linear graph was used to determine the rate of enzyme reaction at each concentration of inhibitor.

The results were expressed as, IC$_{50}$ values, the IC$_{50}$ being the concentration of inhibitor required to reduce the activity of the enzyme to 50% of its control value at a substrate concentration of 1.5 micromolar ($^3$H) testosterone for the aromatase enzyme and 7 micromolar ($^{14}$C) cholesterol) for the desmolase enzyme. A. Desmolase The mitochondrial fraction of bovine adrenal cortex provided the source of desmolase and the method of isolation was essentially as published by R. B. Hochberg et al., Biochemistry, 13, 603 (1974). The enzyme activity was assayed using (26-$^{14}$C)-cholesterol as substrate and measuring the $^{14}$C-isocaproic acid released, see R. B. Hochberg et al., supra. and V. I. Uzgiris et al., Endocrinology, 101, 89 (1977). Inhibitor compounds were added in ethanol ( microliters) and an equal volume of ethanol was added to the control assay. The total volume of the assay mixture was 1.0 ml. After preincubating the assay tubes at 30° C. for 5 minutes, the reaction was started by the addition of 1 mg of mitochondrial protein. Samples were removed after 2,4 and 6 minutes of incubation and the assay completed as described. B. Aromatase Aromatase was obtained from the microsomal fraction of human placental tissue, as described by K. J. Ryan, J. Biol. Chem. 234, 268 (1959). Activity was monitored by measuring the $^3$H$_2$O formed from (1,2-$^3$H) testosterone during aromatization, see P. E. Graves et al., Endocrinology, 105, 52 (1979). The assay procedure was as described above, except that the substrate concentration was 1.5 micromolar and after preincubation of the tubes at 30° C. for 5 minutes the reaction was started by the addition of 0.5 mg of microsomal protein. Samples were taken after 5, 10 and 15 minutes of incubation.

Results are shown in Table 1 below. 3-Ethyl-3-(4-pyridyl)-glutarimide is a potent competitive inhibitor in vitro of aromatase activity. The 2- and 3-pyridylglutarimide analogues display no inhibitory action towards aromatase. All three pyridylglutethimide compounds are inactive as inhibitors of desmolase activity.

TABLE 1

Inhibitory power of glutarimide derivatives versus aromatase and desmolase

[Structure: glutarimide with Et and Ar substituents at 3-position]

| Compound, Ar | IC$_{50}$ micromolar concentrations | |
|---|---|---|
| | Aromatase | Desmolase |
| 4-aminophenyl | 7 | 30 |
| 4-pyridyl | 10 | None |
| 2-t-butyl-pyridyl | 20 | None |
| 3-pyridyl | None | None |
| 2-pyridyl | None | None |

Tests in vivo on tumour regression

Rat mammary tumours induced with MNU (N-methyl-N-nitrosourea) have been shown to be hormone-responsive in that they contain oestrogen receptor and regress on oophorectomy, see Gullino et al., JNCI 54, 40 (1975) and Williams et al., JNCI, 66, 147 (1981).

Unlike DMBA (7,12-dimethylbenz[a]anthracene) induced tumours, MNU tumours may be primarily oestrogen-, rather than prolactin-dependent, see Pruitt, Rose and Bryan, Proc. Ann. Cancer Res. 20, 87, (1979). For this reason, the MNU model was chosen to assess the effect of 3-ethyl-3-(4-pyridyl)glutarimide on tumour growth in vivo.

Using the method of Williams et al., supra, mammary tumours were induced in virgin female rats of the inbred strain Ludwig Wistar/Ola (WF/ICRF/Ola) by intravenous administration of MNU. MNU was dissolved in 0.9% aqueous sodium chloride solution acidified to pH 5 with acetic acid. Starting at age 50 days, each rat received 3 injections at 14 day intervals via the tail vein (5 mg MNU/100 g body weight/injection; injection volume of 0.5 ml/rat). Animals were assigned to experimental groups at 125-140 days after the first injection, with 12 animals in each group. At this time they bore from 1-3 tumours per animal.

Aminoglutethimide and 3-ethyl-3-(4-pyridyl)glutarimide were dissolved in dimethyl sulphoxide (19 mg/ml) and subcutaneous injections given to each rat of 0.165 millimoles/kg body weight/day, via two equal injections morning and evening. Controls received equivalent injections of DMSO alone.

Aminoglutethimide and 3-ethyl-3-(4-pyridyl)flutarimide were administered for a 42 day period and at the end of this time tumours were again measured. Results were expressed in terms of the percentage of initial tumour volume for each tumour after 42 day, treatment. Table 2 below shows the number of tumours which are unchanged in volume, have regressed and have grown. The results indicate that treatment with aminoglutethimide causes an increase in the percentage of tumours which regress. 3-Ethyl-3-(4-pyridyl)glutarimide shows a similar effect. In both treatment groups, a greater proportion, compared with controls of tumours which do not regress, shows an increase in volume of less than 100%.

It would appear that 3-ethyl-3-(4-pyridyl)glutarimide is at least as effective an inhibitor of tumour growth in this assay as aminoglutethimide.

TABLE 2

| | No. tumours in each class after 6 weeks | | | | |
|---|---|---|---|---|---|
| | Regressed by 50% or more | Regressed but by less than 50% | No change | Grown by up to 100% | Grown by more than 100% |
| Control | 2 | 2 | 1 | 1 | 10 |
| Aminoglutethimide | 4 | 3 | 0 | 2 | 5 |
| 3-Ethyl-3-(4-pyridyl)glutarimide | 9 | 3 | 1 | 6 | 8 |

Tests on animals

Tests were carried out to study the activity on the central nervous system of 3-ethyl-3-(4-pyridyl)glutarimide (hereinafter "PyG") compared with 3-ethyl-3-(4-aminophenyl)glutarimide, also known as aminoglutethimide, (hereinafter "APG"), with chlorpromazine (hereinafter "CPZ") and with a blank control.

Male and female HPG (normal) mice, 8-12 weeks old, were used. All drugs were injected intraperitoneally.

A solution of APG was prepared by dissolving 40 mg in 0.9 ml M HCl and adding M NaOH to raise the pH to 3.5-4. The volume was made up to 2 ml with deionized water. If the solution was left for longer than 2 hours the salt precipitated out again. This was remedied by heating and mixing until it dissolved. A solution of PyG was prepared by dissolving 50 mg in 0.9 ml M HCl. This went into solution at low pH very nicely. M NaOH was added to pH 3.5-4. The volume was made up using deionized water. The salt was not stably dissolved and came out of solution within 15 minutes. It was necessary to keep the solution heated and it often had to be injected while still warm. For the control solution 9 parts by volume of M HCl were added to 2 parts by volume of deionized water and brought up to pH 3.5-4 with M NaOH.

Studies on anticonvulsant properties: The mice were pre-treated with the test compound or control and then placed in individual cubicles and observed for any convulsant activity induced by the analeptic agent pentylenetetrazol (50 mg/kg). Pentylenetetrazol, when administered after an injection of NaCl vehicle, produced a characteristic series of activities within 5 minutes of injection. Increased motor activity was followed by tonic convulsions, then severe clonic extensor convulsions which caused death. APG, as expected, prevented convulsions. PyG was tested at doses of 400 mg/kg, 300 mg/kg and 200 mg/kg. None of these doses prevented the pentylenetetrazol-induced convulsions.

Rotating rod experiments: After administration of the test compound or control, each mouse was tested for drug-induced ataxia by the rotarod test. A kymograph was used, placed on its side. Tests were performed at speeds of 1 r.p.m. and 3 r.p.m. The number of falls per 2 minutes interval was recorded 15 minutes and 30 minutes after injection.

The results obtained at the two different speeds showed a close correlation. For both APG and PyG the peak effect appeared 15 minutes after injection. APG had a pronounced effect on motor co-ordination. Most of the mice were heavily sedated and thus completely unable to maintain themselves on the rod at either speed. PyG at a dose of 300 mg/kg showed little difference from the control. At the higher dose of 400 mg/kg the mice became more rigid, and while falling off the faster rod more frequently they tended to slump round the slowly rotating rod, and so stay on for a longer time. This same kind of effect was seen with the chlorpromazine-treated mice, which were considerably sedated.

TABLE 3

| | | Results from the rotarod test. | | | | |
|---|---|---|---|---|---|---|
| DRUG DOSE (mg/kg) Falls/2 min | | CONTROL | PyG 400 | PyG 300 | APG 100 | CPZ 10 |
| 1 r.p.m. | 15 min | 0 | 0.8 ± 0.4 | 0.6 ± 0.3 | 18.5 ± 3.5 | 3.5 ± 0.6 |
| | 30 min | 0 | 0.4 ± 0.2 | 0 | 4.8 ± 2.0 | 8.5 ± 0.6 |
| 3 r.p.m. | 15 min | 1.2 ± 0.3 | 4.8 ± 1.0 | 1.5 ± 0.5 | 27.0 ± 2.0 | 4.5 ± 1.4 |
| | 30 min | 1.1 ± 0.4 | 3.6 ± 1.3 | 2.0 ± 0.2 | | 11.0 ± 2.5 |

Behavioral observations: The comprehensive observational assessment of drug-induced behavioral activity described by S. Irwin, Psychopharmacologia 13, 222 (1968) was used. The mice treated with test compound or control were subjected to the following tests.

Passivity: The mice were placed in unusual positions such as being suspended vertically by either fore or hindlimbs in an attempt to assess for any diminution of the normal struggle response. This test was carried out 20-30 minutes after injection and the mice were scored on a rating of 0-4. A score of 0 indicated no diminution of the struggle response as found in the normal untreated animal. 4 represented the severely cataleptic or hypnotic state observed with some of the treatments.

Reflexes: The righting reflex was tested to see whether or not the animal could right itself if turned over. The corneal reflex was assessed by testing for eye blinking when the end of a matchstick was brought near the eye. The flexor reflex was tested by pinching the mouse's toe with forceps; withdrawal of the hindlimb indicated a positive result.

The mice were also observed for piloerection, increased grooming activity, tremors, twitches, abnormal gait, abdominal tone and overall spontaneous motor activity.

Any additional abnormal behavior was also noted.

APG (100 mg/kg) caused marked sedation, made obvious by reduced spontaneous motor activity, wobbly movements, staggered gait and diminished struggle response. Corneal, righting and flexor reflexes were still apparent, the flexor reflex being slightly augmented as compared to the untreated animals. 200 mg/kg of APG was administered to three animals and all fell asleep within a few minutes of the injection.

200 mg/kg of PyG produced no grossly observable differences from the control mice. At 300 mg/kg some mice showed slight reduction in spontaneous motor activity and diminished struggle response, but in other respects seemed unaffected by the treatment. At 400 mg/kg all mice were noticeably less active, more passive and had lost some control of their hindlimbs; thus they tended to stagger slightly and move sluggishly. All reflexes were still evident and the augmented flexor reflex, as had been noted with APG and CPZ-treated animals, was not present. A dose of 500 mg/kg of PyG was lethal to the three mice tested.

10 mg/kg chlorpromazine caused complete diminution of the struggle response, sluggish movement and diminished alertness. The muscle rigidity, as seen in these mice, and decreased activity are typical signs of catalepsy. Loss of the righting reflex occurred in 2 out of 6 mice, the flexor reflex was augmented and the corneal reflex was normal. 5 out of 8 mice displayed unpredictable jumping and darting movements, particularly when placed on the rotarod.

TABLE 4

| | Behavioural observations - summary of main effects observed (N = normal, W = wobbly, Dec = decreased, Inc = increased, + = effect present, − = effect absent) | | | | | | | | |
|---|---|---|---|---|---|---|---|---|---|
| TREATMENT | PASSIVITY | RIGHTING REFLEX | GROOMING | TREMORS | TWITCHES | ABNORMAL GAIT | MOTOR ACTIVITY | FLEXOR REFLEX | CORNEAL REFLEX |
| 100 mg/kg PyG | 3 | + | + | − | − | W | Dec | Inc | + |
| 200 mg/kg | 0 | + | − | − | − | − | N | + | + |
| 300 mg/kg | 1-0 | + | + | − | − | − | N | + | + |
| 400 mg/kg | 3 | + | + | − | − | W | Dec | + | + |
| CPZ 10 mg/kg | 4 | − | − | − | − | − | Dec | Inc | + |
| Control | 0 | + | − | − | − | − | N | + | + |

We claim:

1. 3-Ethyl-3-(4-pyridyl)glutarimide and derivatives thereof, of the formula

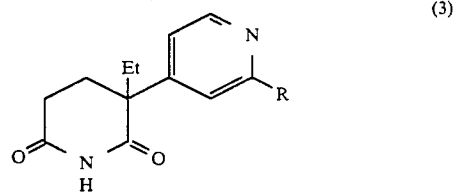

wherein R represents a hydrogen atom or an alkyl group having 1 to 4 carbon atoms, in the form of an optical isomer or a mixture of optical isomers, and their therapeutically acceptable acid addition salts.

2. A pharmaceutical composition for treating mammals suffering from oestrogen-dependent breast tumours comprising a therapeutically effective amount of a compound claimed in claim 1 in association with a pharmaceutically acceptable carrier or diluent.

3. A method of treating mammals suffering from oestrogen-dependent breast tumours, which comprises administering to the sufferer a therapeutically effective amount of a compound according to claim 1.

4. The compound according to claim 1, wherein R is hydrogen.

5. The compound according to claim 1, wherein R is t-butyl.

6. The composition according to claim 2, wherein R is hydrogen or t-butyl.

7. The method according to claim 3, wherein R is hydrogen.

8. The method according to claim 3, wherein R is t-butyl.

* * * * *